United States Patent
Grund et al.

(10) Patent No.: US 9,743,670 B2
(45) Date of Patent: Aug. 29, 2017

(54) METHOD OF TREATING WATER WITH CHLORINE DIOXIDE

(71) Applicant: INFRACOR GmbH, Marl (DE)

(72) Inventors: Gerda Grund, Coesfeld (DE); Hartmut Rahtz, Duelmen (DE); Hermann-Josef Korte, Haltern am See (DE)

(73) Assignee: Infracor GmbH, Marl (DE)

( * ) Notice: Subject to any disclaimer, the term of this patent is extended or adjusted under 35 U.S.C. 154(b) by 42 days.

(21) Appl. No.: 14/351,377

(22) PCT Filed: Oct. 11, 2012

(86) PCT No.: PCT/EP2012/070115
§ 371 (c)(1),
(2) Date: Apr. 11, 2014

(87) PCT Pub. No.: WO2013/053789
PCT Pub. Date: Apr. 18, 2013

(65) Prior Publication Data
US 2014/0302176 A1    Oct. 9, 2014

(30) Foreign Application Priority Data
Oct. 14, 2011  (EP) .................................. 11185154

(51) Int. Cl.
*A01N 59/00* (2006.01)
*C01B 11/02* (2006.01)
*C02F 1/76* (2006.01)

(52) U.S. Cl.
CPC ............ *A01N 59/00* (2013.01); *C01B 11/024* (2013.01); *C02F 1/76* (2013.01)

(58) Field of Classification Search
CPC ................................. C01B 11/024; C02F 1/76
See application file for complete search history.

(56) References Cited

U.S. PATENT DOCUMENTS

| | | |
|---|---|---|
| 6,506,248 B1 | 1/2003 | Duselis et al. |
| 2005/0244328 A1 | 11/2005 | Schmitz et al. |
| 2009/0159538 A1 | 6/2009 | Duve |
| 2010/0155341 A1* | 6/2010 | Duve .................... A01N 59/00 210/756 |
| 2011/0220587 A1 | 9/2011 | Duve |
| 2012/0000862 A1 | 1/2012 | Belluati et al. |
| 2014/0021141 A1 | 1/2014 | Grund et al. |
| 2014/0302176 A1 | 10/2014 | Grund et al. |

FOREIGN PATENT DOCUMENTS

| | | |
|---|---|---|
| DE | 10 2006 060 578 A1 | 6/2008 |
| DE | 10 2008 042 424 A1 | 6/2009 |
| JP | 10-81503 A | 3/1998 |
| JP | 2001-518867 A | 10/2001 |
| JP | 2011-506087 A | 3/2011 |
| JP | 2011-508661 A | 3/2011 |
| WO | WO 2009/077160 A1 | 6/2009 |

OTHER PUBLICATIONS

The Essentail Chemical Industry onlline (Hydrogen chloride. Mar. 18, 2013. http://www.essentialchemicalindustry.org/chemicals/hydrogen-chloride.html).*
Search Report issued Mar. 6, 2012 in European Patent Application No. EP 11 18 5154 (with English translation of Category of Cited Documents).
International Search Report issued Jan. 21, 2013 in PCT/EP2012/070115.
Office Action issued Jan. 18, 2016 in Japanese Patent Application No. 2014-535064 (with English language translation).

* cited by examiner

*Primary Examiner* — Anna Falkowitz
(74) *Attorney, Agent, or Firm* — Oblon, McClelland, Maier & Neustadt, L.L.P.

(57) ABSTRACT

The present invention relates to a method of preparing chlorine dioxide ($ClO_2$) from hydrochloric acid (HCl) and sodium chlorite ($NaClO_2$) in the presence of water ($H_2O$). The invention has for its object to further develop the method such that it is more economical to install and operate. The object is achieved when the hydrochloric acid is used in aqueous solution at a concentration of 27 to 33 wt %, the sodium chlorite is used in aqueous solution at a concentration of 22 to 27 wt % and the molar ratio of hydrochloric acid used to sodium chlorite used is between 2.14 and 4.2.

3 Claims, 4 Drawing Sheets

METHOD OF TREATING WATER WITH CHLORINE DIOXIDE

CROSS REFERENCE TO RELATED APPLICATIONS

The present application is a 35 U.S.C. §371 national stage patent application of International patent application PCT/JP2012/077544, filed on Oct. 25, 2012, published as WO/2013/062028 on May 2, 2013, the text of which is incorporated by reference, and claims the benefit of the filing date of Japanese application nos. 2011-233817, filed on Oct. 25, 2011, and 2011-263353, filed on Dec. 1, 2011, the text of each of which is also incorporated by reference.

The invention relates to a method of preparing chlorine dioxide ($ClO_2$) from hydrochloric acid (HCl) and sodium chlorite ($NaClO_2$) in the presence of water ($H_2O$), and also to a method of treating water with chlorine dioxide prepared from hydrochloric acid and sodium chlorite.

Methods of this type are known from WO2009/077309A1.

Chlorine dioxide ($ClO_2$) is an explosive and extremely toxic chemical used as a biocide to disinfect water. Tap water, drinking trough water, rinsing or cleaning water in the food industry or biomedical engineering, swimming pool water or industrial-process water such as cooling water for example may be concerned.

To kill off microorganisms such as germs, bacteria, viruses, fungi or algae in the water, a low concentration of about 0.2 g of chlorine dioxide in one liter of water is sufficient.

As chlorine dioxide also has a bleaching effect, water can also be enriched with chlorine dioxide for the purpose of producing a bleaching agent. Such a bleaching agent can be used to bleach pulp in papermaking for example. The concentrations for this are different than the biocide treatment.

Owing to the explosiveness of gaseous chlorine dioxide ($c>300$ g/m$^3$) and aqueous chlorine dioxide solutions ($c>26$ g/l), chlorine dioxide cannot be stored in compressed form or in solutions having comparatively high concentrations. Against this background, chlorine dioxide is ideally prepared at the site of use. This is accomplished by contacting reactive foundationstock chemicals in specific reactors of chlorine dioxide generator plants. The chemical stock reservoir vessels, the metering devices and the reactor of the chlorine dioxide plants combine to form a single, localized piece of equipment, which is generally accommodated in rooms to which people have access. A general introduction into the chlorine dioxide treatment of cooling water is: Nowosielski, Marek: On-Site Chlorine dioxide: A Review of Uses, Safety and New Processes. Official Proceedings—65th International Water Conference (2004), pages 213-225.

More recent endeavours seek to synthesize the chlorine dioxide in situ, i.e. directly in the water to be treated. This approach makes for maximum possible process safety. Examples appear in the patent literature under WO2009/077309A1, WO2009/077160A1, DE202004005755U1 and US2005/0244328A1.

Different ways to synthesize chlorine dioxide are known. On an industrial scale, chlorine dioxide is often produced from sodium chlorite or sodium chlorate using hydrochloric acid, chlorine or sulphuric acid/hydrogen peroxide. The latest commercial processes use sodium chlorite as one of the starting materials.

In what follows, the basic chemistry of the most common processes for producing chlorine dioxide is described. The chemicals used are known as feed chemicals or else as reactants. The chemicals which are formed are called products. Chlorine dioxide is always the target product, but by-products are formed as well.

1. Process Involving Sodium Chlorite and a Strong Acid

The first process uses a strong acid together with sodium chlorite ($NaClO_2$). The strong acid is usually hydrochloric acid (HCl) or sulphuric acid ($H_2SO_4$). When hydrochloric acid is used, the reaction stoichiometry reads as follows:

$$5NaClO_2+4HCl \rightarrow 4ClO_2+5NaCl+2H_2O \quad \text{[equation 1]}$$

Chlorine dioxide can also be formed by using sulphuric acid in accordance with the following reaction:

$$10NaClO_2+5H_2SO_4 \rightarrow 8ClO_2+5Na_2SO_4+2HCl+4H_2O \quad \text{[equation 2]}$$

By-products in either process are the water of reaction and the particular salt of the particular acid used. The reactants are always used in aqueous solution. The products are accordingly likewise present in aqueous solution. The influent and effluent water of solution and the water of reaction, i.e. the water formed in the reaction, are not the water to be treated within the meaning of the invention. Any reference to water here is to be understood as meaning a collective term for the water to be treated, water of solution, water of reaction and any water of dilution.

2. Process Proceeding from Sodium Chlorite and Chlorine

This process uses gaseous chlorine ($Cl_2$) together with sodium chlorite. The reaction proceeds in two stages, initially to form hydrochloric acid.

$$Cl_2+H_2O \rightarrow HOCl+HCl \quad \text{[equation 3]}$$

The intermediate, hypochlorous acid (HOCl), then reacts with sodium chlorite ($NaClO_2$) to form chlorine dioxide ($ClO_2$).

$$HOCl+HCl+2NaClO_2 \rightarrow 2ClO_2+2NaCl+H_2O \quad \text{[equation 4]}$$

The stoichiometric reaction from the two equations is:

$$Cl_2+2NaClO_2 \rightarrow 2ClO_2+2NaCl \quad \text{[equation 5]}$$

3. Process Proceeding from Sodium Chlorite and Sodium Hypochlorite

The third process uses sodium hypochlorite (NaOCl) together with sodium chlorite:

$$NaOCl+HCl \rightarrow NaCl+HOCl \quad \text{[equation 6]}$$

$$HCl+HOCl+2NaClO_2 \rightarrow 2ClO_2+2NaCl+H_2O \quad \text{[equation 7]}$$

These synthesis reactions to produce chlorine dioxide are all generally carried out in reactors in either continuous or batch operation.

The present invention relates exclusively to the synthesis route of equation 1.

Nowosielski mentions in his abovementioned paper that the chlorite/hydrochloric acid process is typically carried out with a 250% excess of hydrochloric acid. Since the stoichiometric ratio of sodium chlorite to hydrochloric acid is 4:5=0.8 according to equation 1, a 250% excess of hydrochloric acid results in a molar ratio of 250%*0.8=2 for hydrochloric acid to sodium chlorite. Commercially available reactors would accordingly achieve chlorine dioxide yields of 90%.

A particularly advantageous way to perform the biocide treatment of industrial cooling water is by the sodium chlorite/hydrochloric acid method described in WO2009/077309A1. The highly concentrated use of reactants which is taught therein makes for very effective disinfection of water treated. In situ synthesis makes the method very safe. Where this method is in need of improvement is with regard to its economics: the amount of reactants used and the chlorine dioxide yield achieved therewith are chiefly determinative of process costs; the level of capital costs for the plant is dictated by component size, especially by the size of the chlorine dioxide reactors.

In view of this prior art, the present invention has for its object to further develop the tried and tested hydrochloric acid/chlorite process such that it is more economical to install and operate.

This object is achieved when
a) the hydrochloric acid is used in aqueous solution at a concentration of 27 to 33 wt %;
b) the sodium chlorite is used in aqueous solution at a concentration of 22 to 27 wt %;
c) and the molar ratio of hydrochloric acid used to sodium chlorite used is between 2.14 and 4.2.

The present invention accordingly provides a method of preparing chlorine dioxide from hydrochloric acid and sodium chlorite in the presence of water, in which the hydrochloric acid is used in aqueous solution at a concentration of 27 to 33 wt %, the sodium chlorite is used in aqueous solution at a concentration of 22 to 27 wt % and the molar ratio of hydrochloric acid used to sodium chlorite used is between 2.14 and 4.2.

It was found that the molar ratio of hydrochloric acid and sodium chlorite has an influence on the yield and the reaction rate of chlorine dioxide synthesis; and that the optimum molar ratio is dependent on reactant concentration.

According to equation 1, the stoichiometric molar ratio of hydrochloric acid to sodium chlorite is 4:5=0.8. When the amount of the acid used is increased, the yield of the target product (chlorine dioxide) also increases. This behaviour is observed until maximum yield (100%) is reached. But any further increase in the amount of the acid (beyond a certain amount) unexpectedly leads to a reduced yield.

This dependency can be observed on both concentrated acid (30%) and dilute acid (20%). This effect of the appearance of the maximum is observable irrespective of any residence-time setting.

The particular choice of operating parameters accordingly rests on the actually surprising realization that the yield of chlorine dioxide does not rise constantly as reactant concentration is increased while at the same time an excess of hydrochloric acid is maintained, but that there is a relatively low optimum for both process parameters, so this is not a case of "the more, the better". This realization makes it possible to run the process with a comparatively low reactant feed and yet obtain a high yield of chlorine dioxide and hence achieve the disinfection task. Operating costs are reduced as a result. The claimed ranges lead to yields above 93%, while even complete conversions are obtained over wide ranges.

It is further surprising that the reaction in the operating range of the present invention proceeds at a previously unknown high rate—this knowledge makes it possible to conduct the reaction with distinctly shorter residence times and hence in smaller reactors:

This is because the residence time t in the case of continuous reactions is defined as the ratio of reactor volume V to volume flow V' through the reactor:

$$t=V/V' \qquad \text{[equation 8]}$$

If, then, the reaction proceeds at a faster rate, it is accordingly possible to reduce the reactor volume V for the same throughput V'. Smaller reactors are less costly. Hence performing the chlorine dioxide synthesis in the manner of the present invention makes for high time-specific productivity and so reduces not only the operating but also the capital costs of the chlorine dioxide plant.

The synthesis of chlorine dioxide from concentrated feed chemicals combined with a stoichiometric excess of acid leads to an increased reaction rate. In the molar ratio range found therein, the rate can be increased such that the residence time needed to obtain the maximum yield drops to values below 6 seconds. Hence reactor residence time of reactants is preferably less than 6 seconds, especially 5 seconds.

Preferably, the hydrochloric acid is used in aqueous solution at a concentration of 30 wt %. The optimum concentration of sodium chlorite in water is 25 wt %.

The optimum molar ratio of hydrochloric acid used to sodium chlorite used is between 2.19 and 3.6 for the aforementioned optimum reactant concentrations. The conversion and rate maximum and hence the maximum possible process intensification is obtained at a molar $HCl:NaClO_2$ ratio of about 3. In view of the technical tolerance/control range, therefore, the process should be run using a molar ratio between 2.4 and 3.4 for hydrochloric acid used to sodium chlorite used. This range is therefore particularly preferable.

The method according to the invention is preferably conducted in a reactor surrounded by water. A reactor immersed in water enhances process safety: since the two reactants first come into contact with each other in the reactor, the hazardous chlorine dioxide is only formed in the immersed reactor and hence under water. In the event of an accident, the water surrounding the reactor will instantly dilute the chlorine dioxide, limiting the threat to the environment.

In a preferred further development of the invention, the chlorine dioxide emerging from the reactor in aqueous solution is diluted with water and then mixed with the water surrounding the reactor. This procedure makes it possible for the concentration of chlorine dioxide in the water to be treated to be adjusted in a controlled manner with dilution water whereby the chlorine dioxide is ultimately flushed into the water to be treated.

The chlorine dioxide concentration on exit from the reactor should be above 3 g/l of solution preferably above 26 g/l of solution and more preferably above 80 g/l of solution. Exceeding the explosion limit of 26 g/l is only possible when the aqueous chlorine dioxide emerging from the reactor is immediately diluted with the water of dilution and/or the reactor sits immersed in water. The high concentration of chlorine dioxide is due to the high process intensification.

The chlorine dioxide produced according to the invention is preferably used for disinfection/biocidal treatment of water of any kind. The invention accordingly also provides a method of treating water with chlorine dioxide comprising the steps of:
a) providing water to be treated;
b) providing a reactor;
c) immersing the reactor in the water to be treated;
d) providing hydrochloric acid in aqueous solution outside the water to be treated;
e) providing sodium chlorite in aqueous solution outside the water to be treated;
f) conveying the aqueous hydrochloric acid and the aqueous sodium chlorite into the reactor;
g) reacting the aqueous hydrochloric acid and the aqueous sodium chlorite in the reactor to form chlorine dioxide in aqueous solution;
h) mixing the aqueous chlorine dioxide with the water to be treated;

i) wherein the hydrochloric acid is provided in aqueous solution at a concentration of 27 to 33 wt %;

k) wherein the sodium chlorite is provided in aqueous solution at a concentration of 22 to 27 wt %;

l) and wherein the molar ratio of hydrochloric acid used to sodium chlorite used is between 2.14 and 4.2.

Storing the feed chemicals hydrochloric acid and sodium chlorite in separate containers outside the water is comparatively unconcerning and readily manageable.

Optimum process parameters were described above.

A plant for conducting the method according to the invention typically includes two separate tanks for the feed chemicals, one for the sodium chlorite and one for the hydrochloric acid. Fitments are provided to feed the reactants into the respective storage tanks and also to withdraw solutions therefrom. The reactants need not be introduced into the tanks in the concentration used according to the present invention. If desired, the requisite concentration is first set in the tank, for example by adding water of dilution.

These fitments preferably include pumps and feed lines sufficient to ensure the volume flows of feed chemicals. Those skilled in the art are readily able to determine suitable sizes for the storage tanks, feed lines and pumps in question in order that the required feed rates of reactant solutions may be achieved. Pumps are particularly important for the reactants, since they are used to set the molar ratio desired for the reactants. This is accomplished in practice via pump speeds. Some pump designs also make it possible to adjust the conveyed volume stream while keeping the speed constant by adjusting the suction volume or the like for example. But that is more complicated. The suction volume of a pump is the volume conveyed per revolution of the drive and in the case of a piston pump corresponds to the term 'capacity' used by engine builders.

The apparatus further comprises a fitment for bringing the solution of feed chemicals into contact. This fitment is termed a reactor. Any fitment whereby the aforementioned solutions become sufficiently mixed can be used, including conventional T-pieces or other connecting elements to combine two or three streams into one stream, throttle lines and/or a stirred vessel. The aqueous reaction solution, after mixing, can then be fed into the reaction space. The two reactants are preferably contacted in the reaction space. The mixing process can be initiated by any appliance, for example baffle plates, injectors or packings, that is capable of ensuring optimum mixing.

The reaction space used can be any reactor capable of inducing the reaction between the feed chemicals especially the aqueous acid solution and the alkali metal salt of a chlorite ion, including continuous stirred reactors, simple tanks, mass-flow or plug-flow reactors and tubular reactors. A tubular reactor is particularly preferable, since it permits a continuous reaction in a steady state. Normally, a chlorine dioxide generator unit will consist of one tubular reactor only, but a unit's productivity can be enhanced by assembling two or more reactors in a parallel arrangement to form a tube bundle for example. The reactor may be not only temperature-controlled, but also consist of an efficiently heat-conducting material in order that evolved heat of reaction may pass into the surrounding water. The reactor is constructed of materials which exhibit good stability to the particular reaction solutions. Useful reactor materials to generate chlorine dioxide solutions having concentrations of above 28 g/l include, for example, titanium, alloy 31, glass or synthetics e.g. polymers such as PVDF or PTFE for example. The $ClO_2$ is removed from the reactor by any desired mechanism capable of removing an aqueous solution from a reactor. The reaction is preferably carried out in a continuous manner and $ClO_2$ is removed from the reactor in a continuous manner. After leaving the reactor, the $ClO_2$ is metered directly into the water which is to be treated, or transported to one or more other locations via an exit line connected to the reactor outlet.

Using a tubular reactor is preferred in the present invention. In general, the tube of the tubular reactor is designed to be sufficiently long to ensure the envisaged residence time in the reactor in order that the best possible conversion may be achieved for the constituents given the reaction solution flow rate, the reaction solution reactant concentration and the reaction solution temperature. A (temperature-controlled) tubular reactor containing one or more tubular coils is a particularly preferable reactor for forming a suitable on-site generator of aqueous chlorine dioxide. Those skilled in the art are able to size and shape the reactor according to the amount of aqueous chlorine dioxide to be produced, reactant flow rate and concentration, the aqueous reaction solution pH, the $ClO_2$ pH and the reactor temperature. Those skilled in the art are likewise able to modulate the reactor temperature appropriately.

The molar ratio R of hydrochloric acid to the sodium chlorite used for given fixed concentrations of reactant solutions is adjusted via the reactant volume streams $V_{HCl}$ and $V_{NaClO2}$:

$$R = V_{HCl}/V_{NaClO2} * \rho_{HCl}/\rho_{NaClO2} * M_{NaClO2}/M_{HCl} * C_{HCl}/C_{NaClO2} \quad \text{[equation 9]}$$

where

R is the molar ratio of hydrochloric acid to sodium chlorite, $V_{HCl}$ is the volume flow of aqueous hydrochloric acid solution, $V_{NaClO2}$ is the volume flow of aqueous sodium chlorite solution, $\rho_{HCl}$ is the density of aqueous hydrochloric acid solution, $\rho_{NaClO2}$ is the density of aqueous sodium chlorite solution, $C_{HCl}$ is the concentration of aqueous hydrochloric acid solution in wt %, $C_{NaClO2}$ is the concentration of aqueous sodium chlorite solution in wt %, $M_{HCl}$ is the molar mass of hydrochloric acid, $M_{NaClO2}$ is the molar mass of sodium chlorite.

The densities are temperature and concentration dependent. For 30% HCl and 25% $NaClO_2$ they are at 20° C.:

$$\rho_{HCl} = 1.15 \text{ g/cm}^3 \quad \rho_{NaClO2} = 1.2 \text{ g/cm}^3$$

The concentrations are determined by the choice of feed reactants.

$C_{HCl}$=0.3 g HCl/1 g of solution holds for 30% hydrochloric acid solution $C_{NaClO2}$=0.25 g $NaClO_2$/1 g of solution holds for 25% sodium chlorite solution.

The molar masses are natural constants:

$$M_{HCl} = 39.4556 \text{ g/mol} \quad M_{NaClO2} = 90.4415 \text{ g/mol}$$

Using 30% hydrochloric acid and 25% sodium chlorite solutions, it thus follows from equation 9 that the approximate ratio at ambient temperature is:

$$R = 2.64 * V_{HCl}/V_{NaClO2} \quad \text{[equation 10]}$$

The residence time t for a fixed reactor volume V likewise follows from the reactant streams according to equation 8:

$$t = V/(V_{HCl} + V_{NaClO2}) \quad \text{[equation 11]}$$

Not only the molar ratio R of hydrochloric acid to sodium chlorite but also the residence time t can thus be controlled for suitably dimensioned reactor volume V by controlling the reactant volume flows $V_{HCl}$ and $V_{NaClO2}$. The reactant volume flows $V_{HCl}$ and $V_{NaClO2}$ are preferably controlled electrically via the respective metering pump speed.

Remarkably, the factor of 2.64 in equation 10 is pretty much slap bang in the middle of the optimum range for the molar ratio R. Accordingly, when the reactant volume flow rates are made equal ($V_{HCl}/V_{NaClO2}=1$), the system will straightaway operate at an optimum, provided the other prerequisites entered in equation 10 (concentrations, densities) are satisfied. Volume flow rates which are equal are technically very simple to achieve by using identical pumps (equal suction volume) driven by the same shaft at the same speed. As a result, plant hardware and plant software become significantly simpler and hence meaningfully cheaper. The sole precondition then is the use of 30% hydrochloric acid and 25% sodium chlorite at 20° C., which is equal to the usual ambient temperature. Such a plant with coupled reactant-stream control is certainly not as efficient in terms of reactant requirements as a plant with individual reactant-stream control, but does have distinctly lower capital costs and therefore can nonetheless be more economical in certain use scenarios.

The invention accordingly also provides apparatus comprising a sodium chlorite storage tank, a hydrochloric acid storage tank, two pumps for conveying hydrochloric acid in aqueous solution at a first volume flow rate and sodium chlorite in aqueous solution at a second volume flow rate respectively from the respective tanks into a reactor, said apparatus having means whereby the first volume flow rate and the second volume flow rate are equalized. Such apparatus is suitable for conducting the method of the present invention at a molar ratio of R=2.64.

Said means are most simply a conjoint drive for the two pumps via a conjoint shaft at the same speed while the suction volume is chosen to be the same for the two pumps. This purely mechanical construction leads to identical volume flow rates from the two pumps.

The invention also provides for the use of such apparatus for conducting the method of the present invention.

The conductivity value is preferably measured in the solution leaving the reaction space before said solution is delivered to the water which is to be treated. An inductive or optical method of measurement can be used for example. From the conductivity values measured, information is obtainable regarding the chemical conversion of the reactants used and also, where appropriate, in respect of the amount of dilution water used.

The chlorine dioxide solution leaving the reactor outlet or the exit line is diluted such that the renewal rate at the reactor outlet of the water which is to be treated is about 0.1 m³/h to 20 m³/h per gram per hour of chlorine dioxide generated, preferably in the range from 1 m³/h to 4 m³/h per gram per hour of chlorine dioxide generated.

Illustrative embodiments of the invention will now be more particularly described with reference to drawings, where.

Figure 1:
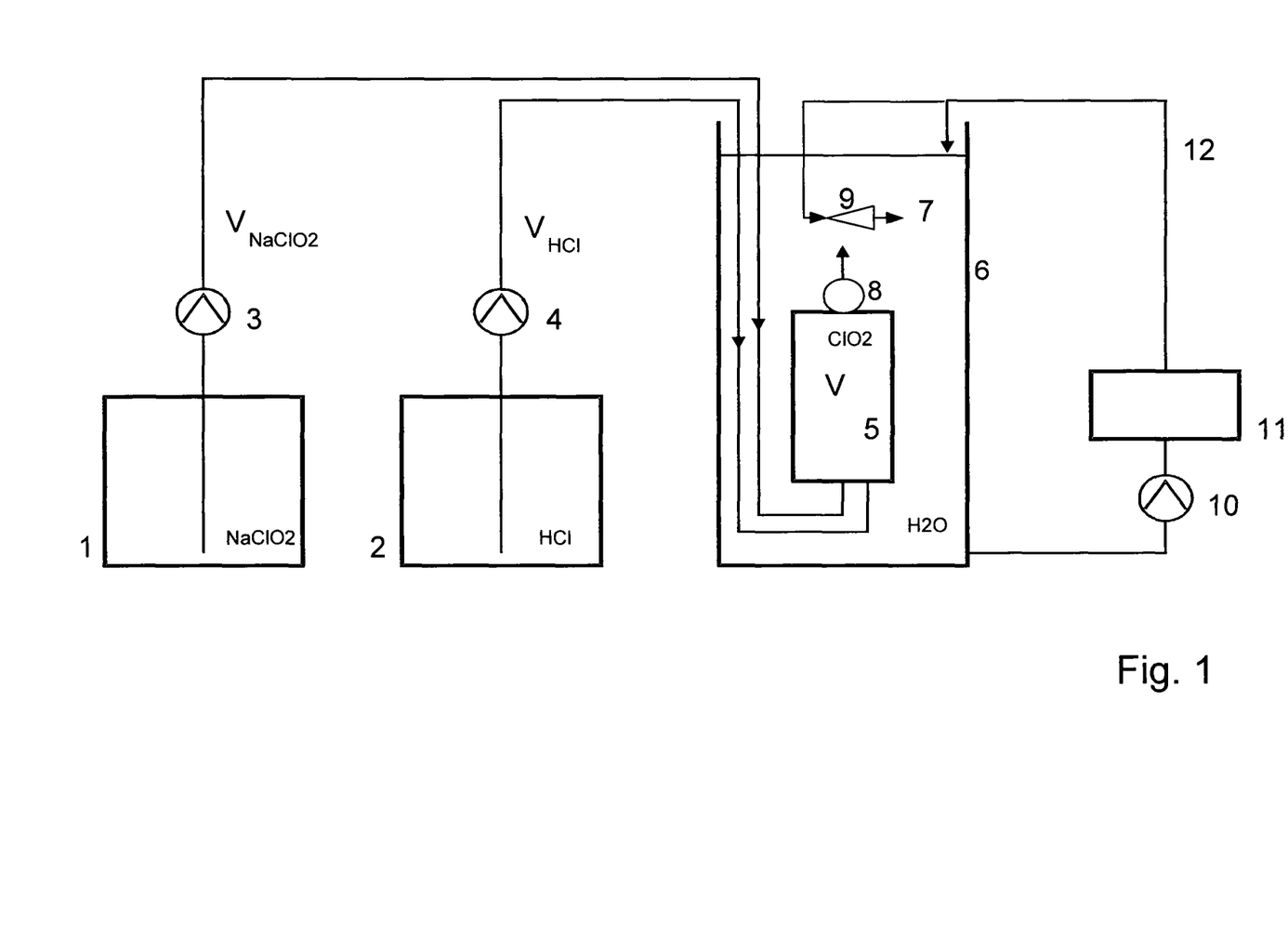
FIG. 1 shows a schematic construction of a plant for conducting the method of the present invention with a reactor immersed in a basin.
Figure 2:
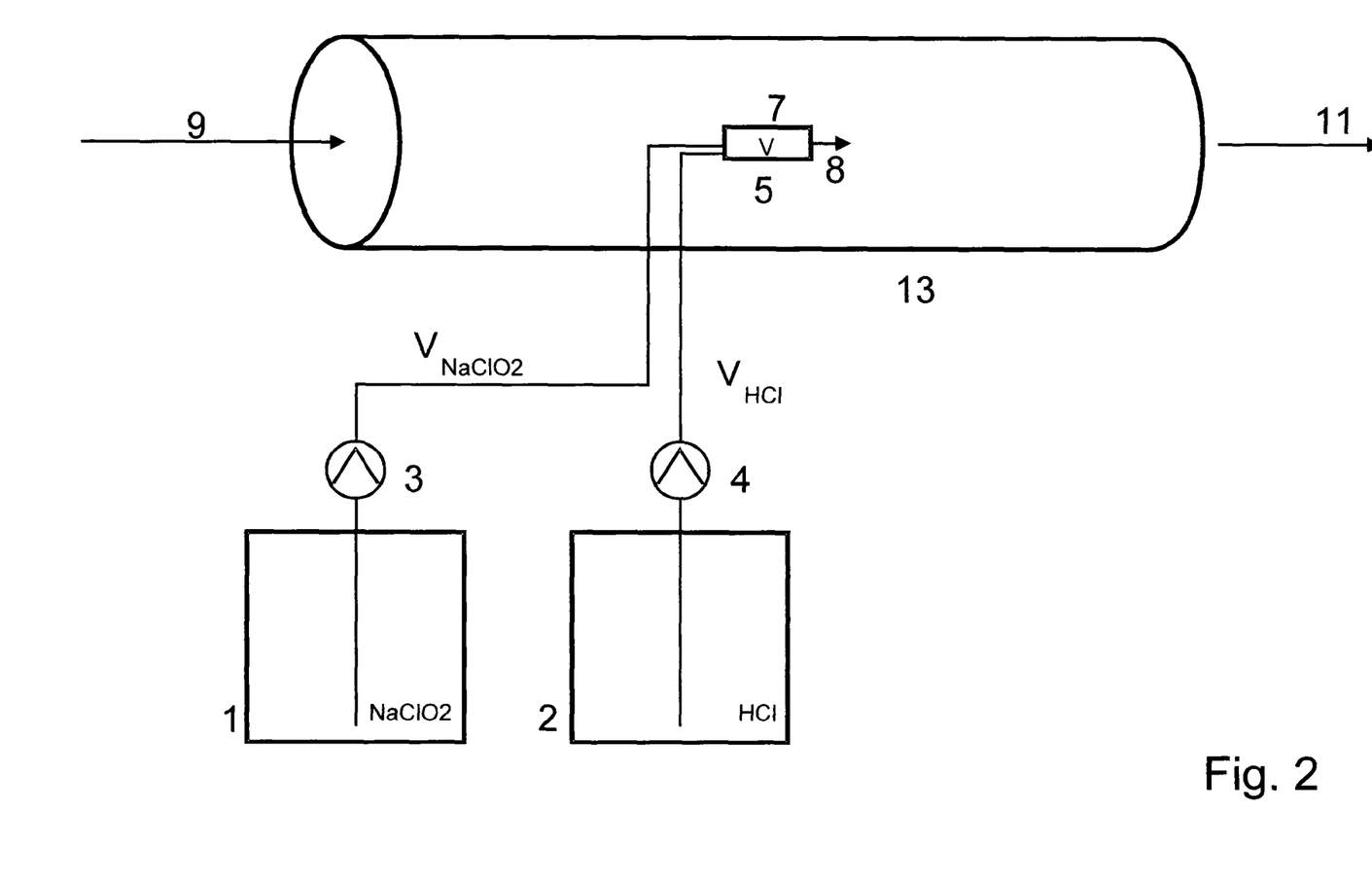
FIG. 2 shows a schematic construction of a plant for conducting the method of the present invention with a reactor inserted in a pipe line.

The method according to the invention can be conducted using for example the apparatuses depicted in FIG. 1 and FIG. 2.

FIG. 1 depicts an in-principle construction for conducting the method of the invention in essentially standing water. The apparatus for treating water with chlorine dioxide comprises two tanks 1 and 2 for the feed chemicals (reactants), a sodium chlorite storage tank 1 with conveyor pump 3 and a hydrochloric acid storage tank 2 with conveyor pump 4. The volume flow rates $V_{HCl}$ and $V_{NaClO2}$ can be adjusted by adjusting the speeds of the two conveyor pumps 3 and 4. The pumps 3 and 4 are connected via individual lines to a reactant inlet on the bottom side of a reactor 5. The reactor contains state of the art appliances to ensure rapid and complete mixing of introduced components in the reaction space. The free volume V in reactor 5 is available as reaction space. By varying the concentration contents of reactant solutions or any dilution water quantity used the resultant chlorine dioxide solution can be adjusted to a concentration of above 3 g/l, preferably above 26 g/l and more preferably to above 80 g/l. The residence time t for reactants in the reactor volume and the molar ratio R of hydrochloric acid to sodium chlorite is controlled via the volume flow rates $V_{HCL}$ and $V_{NaClO2}$.

The reactor 5 is fully immersed in a water-filled basin 6 to ensure, in the event of an accident, immediate dilution of chlorine dioxide produced. The water in the basin is in this case the water 7 which is to be treated.

The upper, opposite end of reactor 5 is equipped with the reactor outlet 8, which is assigned a conductivity measurement.

At the point where the chlorine dioxide solution transfers into the water 7 which is to be treated, a water-jet liquid pump 9 can be arranged to increase the rate at which the water which is to be treated is renewed at the point of chlorine dioxide entry. The feed line from reactor outlet 8 to water-jet liquid pump 9 is in this case equipped with a relief drill-hole to ensure that the pressure of the water 7 that is to be treated takes effect in reactor 5.

The reactor is completely surrounded by the water 7 to be treated, which is standing in basin 6. The treated water is withdrawn from basin 6 via a suction line and fed by a circulation pump 10 to the use site 11. Basin 6 can be a cooling tower basin for example. In that case, use site 11 is a heat exchanger cooled with water which is to be treated. But basin 6 can also be a tap water reservoir. In that case, use site 11 is a manufacturing unit in the biomedical or food industry for example.

Figure 3:
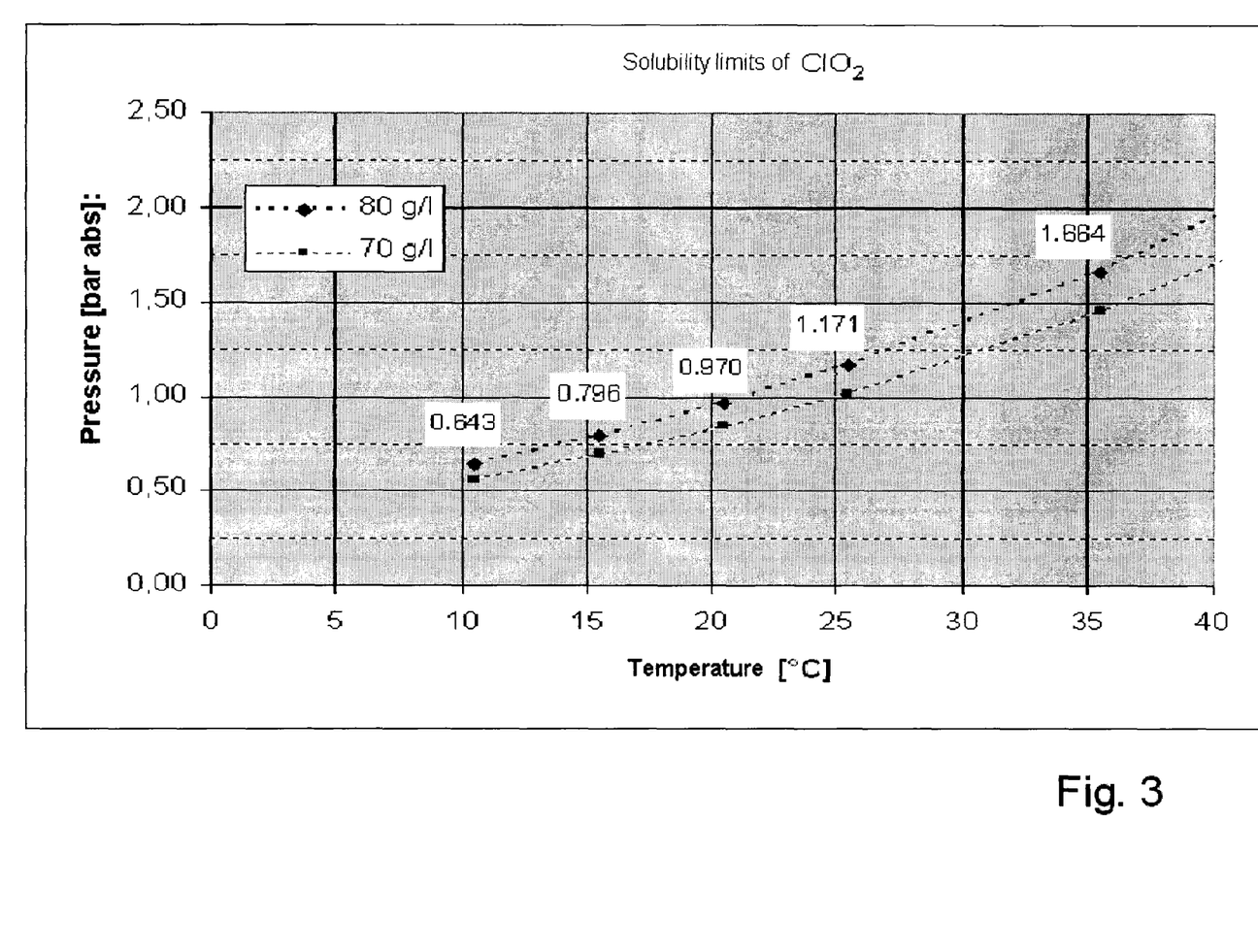
FIG. 3 shows solubility limits of chlorine dioxide in water.

A return line 12 then carries the water 7 to be treated again back into the basin 6 to pass through the reactor outlet 8 again or to be fed into the water-jet liquid pump 9. The reactor outlet 8 can also be positioned close to the suction side of circulation pump 10 in order that rapid exchange at reactor outlet 8 may be ensured of water 7 to be treated. A suitable choice for the parameters "depth of reactor immersion in water to be treated" (pressure) and "concentration of chlorine dioxide solution generated in reactor" having regard to the temperature of the water to be treated, as shown in FIG. 3 by way of example, can be used to prevent the formation of a chlorine dioxide gas phase. An additional possibility is for the chlorine dioxide solution emerging from the reactor 5 to be transported via an exit line connected to reactor outlet 8 (and not depicted in FIG. 1) to one or more than one other location. Assemblies to distribute the chlorine dioxide solution, for example a water-jet liquid pump, a circulation pump, may also be placed there.

A second apparatus for the method of the present invention is shown in FIG. 2. The essential aspect here is that the reactor 5 is positioned within a pipe line 13 through which water 7 to be treated flows, while water to be treated flows around the reaction space V. The water to be treated is thus not standing water but is flowing water. (It will be appreciated that flows can also occur in basin 6, caused especially by the circulation pump 10 or the water-jet pump 9, but the volume in flow is small compared with the overall volume of the basin, and therefore the reference is to standing water there.)

Reactor 5 in FIG. 2 is identically connected to the same feed lines as in FIG. 1. Reactor 5 is likewise surrounded by water 7 which is to be treated, but is positioned within a pipe line 13 through which water 7 which is to be treated flows and which feeds the water 7 to be treated to use site 11 after it has passed through reactor outlet 8.

The molar ratio R of reactants and the residence time t likewise determine the volume flow rates set at the pumps 3 and 4.

More detailed descriptions of suitable equipment for conducting the method of the present invention appear in DE102010027840 in respect of standing water and in DE102010027908 in respect of water flowing through a pipe line.

The concentration of product solution at reactor outlet 8 can rise to above 9 g/l [without water of dilution the $ClO_2$ content rises to 9.1 g/l even on using 3.5% strength reactants], preferably above 26 g/l and more preferably to above 80 g/l of chlorine dioxide, per liter. In this preferred variant, the reactor volume is advantageously minimized. Generally, no further appliances are needed for increasing the renewal rate at reactor outlet 8 of the water 9 which is to be treated in order that the concentration of the chlorine dioxide solution, following entry into the water 7 which is to be treated, may be rapidly shifted from preferably above 80 g per liter into the milligram range. It is likewise generally not difficult to adjust the pressure in pipe line 13 of the water 7 which is to be treated such that the solubility limit of chlorine dioxide is not exceeded in the aqueous solution in reactor 7, as depicted in FIG. 3.

FIG. 3 depicts the solubility limits of chlorine dioxide in an aqueous solution as a function of pressure and temperature, for example for the chlorine dioxide concentrations 70 g/l and 80 g/l.

REACTION EXAMPLES

To demonstrate the effect due to the present invention, an existing chlorine dioxide production plant was run in the course of ongoing operation at two different reaction volumes while varying the reactant molar ratio, the reactant concentration and the residence time and determining the chlorine dioxide conversion achieved in the process. The reaction volume was artificially reduced by introducing glass balls into the reactor. The reactant concentration was varied by adding water to the reactant tank. Residence time and molar ratio were adjusted via the volume flow rate produced by the reactant pumps.

Example 1

Apparatus shown in FIG. 1 is used. The solution in chlorite storage tank 1 contains a 25% strength aqueous sodium chlorite solution and varying amounts of this solution are pumped by conveyor pump 3 into reactor 5. At the same time, varying amounts of a 30% strength aqueous hydrochloric acid solution are likewise fed from acid storage tank 2 into reactor 5 by conveyor pump 4. The reactant temperature was 20° C. After packing with glass balls, the reactor has a free volume V of 13 milliliters and reaction mixture residence time in the reaction space is adjusted via the choice of reactant throughput such that a residence time t of 5 or somewhat less than 5 seconds is obtained at all times [equation 11].

The chlorine dioxide solution emerging from the reactor outlet 8 is continuously mixed, in the water-jet liquid pump 9, with the water 7 which is to be treated, and the mixture is supplied to the disinfection process. After a steady state had become established, samples were taken at the point of exit from the water-jet pump to determine the $ClO_2$ content therein photometrically by measuring the extinction (at 345 nm) and to compute the yield therein. Different HCl and $NaClO_2$ throughputs were established in order that the molar ratio R of feedstocks may be varied from 1.35:1 to 3.46:1. The measured results are reported in Table 1 and plotted using the □ symbol in the diagram of FIG. 4.

Operating at between R=2.84 and 3.19 actually provides complete conversion, i.e. the greatest degree of optimization for the process.

TABLE 1

| HCl 30%; $NaClO_2$ 25%; t = 5 s; V = 13 ml | |
|---|---|
| R [—] | Yield [%] |
| 1.35 | 38.1 |
| 2.14 | 92.5 |
| 2.19 | 93.5 |
| 2.44 | 96.8 |
| 2.51 | 97.7 |
| 2.84 | 100.0 |
| 3.19 | 100.0 |
| 3.46 | 93.8 |

This aqueous $ClO_2$ solution was then additionally admixed in basin 6 with the returned amount of water to be treated. The throughput of water enriched with chlorine dioxide is about 1000 m³ per hour and is pumped by circulation pump 10 out of the basin 6 and to the use site 11. The return of the water 7 to be treated carries the water depleted in chlorine dioxide back into the basin. The reactor outlet 8 is 4 meters below the water in the basin, and the temperature of the water to be treated is up to 32° C.

The apparatus described concerns recooled water 7 in a cooling tower basin (basin 6) from a cooling circuit. The circuit pump 10 pumps the cooling water over heat-exchange surfaces of a chemical manufacturing plant having exothermic sources of heat (use site 11 of treated water) and then trickled over the internals of an evaporative cooling tower before ending up back in the cooling tower basin (basin 6). The cooling tower basin has a capacity of 800 m³. The water level in the intermediate store is under closed-loop level control, so the evaporated cooling water is automatically made up with makeup water.

Example 2

This time the reduced, 13 ml capacity reactor in the same plant was charged with only 20% strength hydrochloric acid and 25% strength sodium chlorite solution. Reactant flow rates were varied to vary the molar ratio of hydrochloric acid to sodium chlorite in the range from 1.24:1 to 5.41:1. Residence time was in each case set to about 5 seconds. The measured results are reported in Table 2 and plotted with the ○ symbol in the diagram of FIG. 4.

TABLE 2

HCl 20%; NaClO$_2$ 25%; t = 5 s; V = 13 ml

| R [—] | Yield [%] |
|---|---|
| 1.24 | 25.5 |
| 2 | 57.6 |
| 2.88 | 86.9 |
| 3.72 | 87.1 |
| 4.7 | 88.0 |
| 5.41 | 90.3 |

Example 3

The glass balls were now removed from the reactor in the same plant. The reactor, the undiminished volume V of which was now 26.67 ml, was again charged with 30% strength hydrochloric acid and 25% strength sodium chlorite solution. Reactant flow rates were varied to vary the molar ratio of hydrochloric acid to sodium chlorite in the range from 0.85:1 to 4.28:1. Residence time was in each case set to about 23 seconds. The measured results are reported in Table 3 and plotted with the Δ symbol in the diagram of FIG. 4.

Complete conversion is achieved between R=2.11 and R=2.59.

TABLE 3

HCl 30%; NaClO$_2$ 25%; t = 23 s; V = 27 ml

| R [—] | Yield [%] |
|---|---|
| 0.85 | 10.7 |
| 1.09 | 61.6 |
| 1.51 | 86.8 |
| 2.11 | 100.0 |
| 2.59 | 100.0 |
| 4.03 | 92.9 |
| 4.28 | 89.0 |

Comparing the conversions obtained in Examples 1 and 2 teaches that increasing the hydrochloric acid concentration causes the conversion of chlorine dioxide to increase (conversions in Example 1 better than in Example 2). In principle, this is not surprising. Crucially, however, conversion increases with increasing hydrochloric acid excess only to then drop off again or only to further increase slowly later. The conversion maximum is located in the range claimed for the molar ratio of hydrochloric acid to sodium chlorite. The technical teaching derivable from that is if possible to exploit the first conversion maximum and to use the more concentrated acid.

Comparing Examples 1 and 3 first confirms once more again the conversion maximum within the claimed range. Surprisingly, there is scarcely any decrease in conversion when residence time is shortened to 5 seconds: complete conversions are also achieved in Example 1. The reaction is accordingly so fast that it has ended after about 5 seconds and hence there is no further conversion. In Example 3, the reactants were accordingly allowed a much too generous residence time. This insight can be technically exploited by reducing the reactor volume V for the same volume flow rate $V'=V_{HCL}+V_{NaClO2}$; cf. Equation 8. The reactor accordingly becomes smaller and cheaper, but achieves almost the same reaction performance, as evidenced by Example 1.

Figure 4:
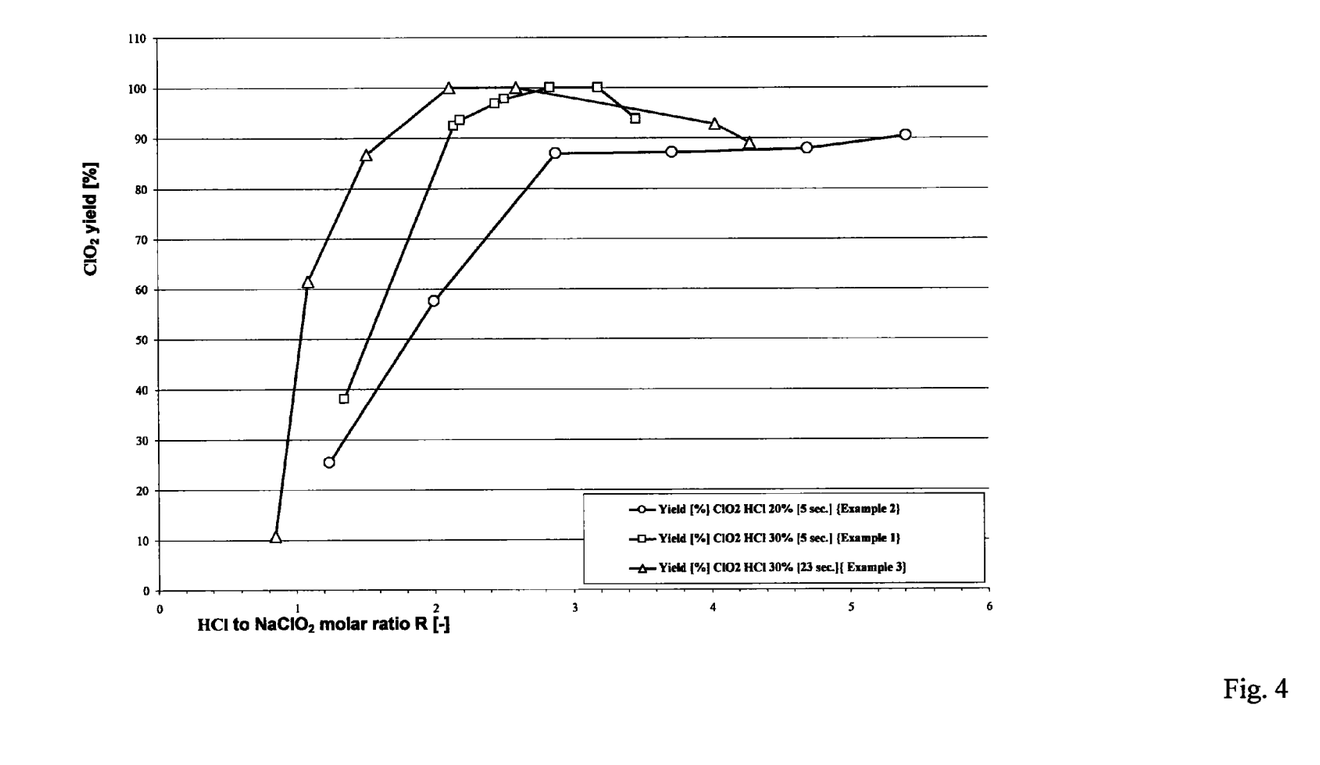
FIG. 4 shows the chlorine dioxide yield as a function of the molar ratio of hydrochloric acid to sodium chlorite.

The results of the three series of tests are plotted in the diagram of FIG. 4. Intermediate values are interpolated. The curves all show a distinct conversion maximum located in the range from 2.14 to 4.2 claimed according to the present invention, preferably between 2.19 and 3.6 and most preferably between 2.4 and 3.4. Conversion here is above 90%, preferably above 93% and most preferably above 96%.

LIST OF REFERENCE NUMERALS

1 sodium chlorite storage tank
2 hydrochloric acid storage tank
3 sodium chlorite conveyor pump
4 hydrochloric acid conveyor pump
5 reactor (reaction space)
6 basin
7 water to be treated
8 reactor outlet
9 water-jet liquid pump
10 circulation pump for water to be treated
11 use site
12 return line
13 pipe line in FIG. 2

The invention claimed is:

1. A method of preparing chlorine dioxide (ClO$_2$), comprising:
   conveying a first aqueous solution of hydrochloric acid comprising 27 to 33 wt % HCl at a controlled rate to a reactor immersed in water;
   conveying a second aqueous solution comprising 22 to 27 wt % sodium chlorite (NaClO$_2$) at a controlled rate to the reactor immersed in water;
   controlling the rates of flow of the hydrochloric acid solution and the sodium chlorite solution such that a molar ratio of the HCl to the NaClO$_2$ in the reactor is from 2.84 to 3.19 reacting the HCl with the NaClO$_2$ in the reactor to obtain a solution of ClO$_2$ at a concentration of 26 g/l or higher; and
   removing the ClO$_2$ solution from the reactor such that a residence time from reaction of the HCl and NaClO$_2$ to removal of the ClO$_2$ solution from the reactor is less than 6 seconds.

2. The method according to claim 1, wherein:
   a) the first aqueous solution comprises 30 wt % of the HCl;
   b) the second aqueous solution comprises 25 wt % of the sodium chlorite; or both a) and b).

3. The method according to claim 1, wherein:
   the chlorine dioxide emerges from the reactor in a third aqueous solution; and
   the third aqueous solution is diluted with water and then mixed with the water surrounding the reactor.

* * * * *